United States Patent
Li et al.

(10) Patent No.: US 7,286,631 B2
(45) Date of Patent: Oct. 23, 2007

(54) METHOD AND APPARATUS FOR TOMOSYNTHESIS IMAGE QUALITY CONTROL

(75) Inventors: Baojun Li, Waukesha, WI (US);
Rowland Saunders, Hartland, WI (US);
John Sandrik, Wauwatosa, WI (US);
Xianfeng Ni, Merton, WI (US)

(73) Assignee: General Electric Co., Schenectady, NY (US)

( * ) Notice: Subject to any disclaimer, the term of this patent is extended or adjusted under 35 U.S.C. 154(b) by 22 days.

(21) Appl. No.: 11/339,067

(22) Filed: Jan. 25, 2006

(65) Prior Publication Data

US 2006/0120506 A1    Jun. 8, 2006

Related U.S. Application Data

(63) Continuation-in-part of application No. 10/755,074, filed on Jan. 9, 2004, now Pat. No. 7,056,020.

(51) Int. Cl.
*A61B 6/00* (2006.01)

(52) U.S. Cl. ..................... 378/21; 378/207

(58) Field of Classification Search ............ 378/21–27, 378/204, 205, 207
See application file for complete search history.

(56) References Cited

U.S. PATENT DOCUMENTS

| | | | |
|---|---|---|---|
| 4,055,771 A * | 10/1977 | Goodenough et al. | ........ 378/18 |
| 5,799,059 A | 8/1998 | Stembridge et al. | |
| 6,409,383 B1 | 6/2002 | Wang et al. | |
| 6,460,003 B1 | 10/2002 | Kump et al. | |
| 6,632,020 B2 | 10/2003 | Kaufhold et al. | |
| 6,811,314 B2 | 11/2004 | Cresens | |
| 7,056,020 B2 * | 6/2006 | Saunders et al. | ........... 378/207 |

* cited by examiner

*Primary Examiner*—Jurie Yun

(57) ABSTRACT

A method and apparatus for tomosynthesis image quality control for a tomosynthesis imaging system. The method and apparatus including: positioning a phantom having an edge of predetermined sharpness at a predetermined angle relative to an imaging plane of an x-ray detector; performing tomosynthesis acquisition and generating one or more slice images using one or more three-dimensional reconstruction algorithms; selecting a slice image to be measured from the one or more slice images; identifying a sharpest edge in the slice image to be measured, wherein the sharpest edge in the slice image to be measured includes the in-focus portion of the phantom; inputting the slice image to be measured and coordinates of the sharpest edge in the slice image to be measured into a modulation transfer function (MTF) algorithm; and, using the MTF algorithm, calculating the in-plane resolution and slice thickness of the slice image to be measured.

29 Claims, 13 Drawing Sheets

METHOD AND APPARATUS FOR TOMOSYNTHESIS IMAGE QUALITY CONTROL

CROSS-REFERENCE TO RELATED APPLICATION(S)

The present patent application is a continuation-in-part and claims the benefit of priority of U.S. patent application Ser. No. 10/755,074, filed on Jan. 9, 2004 now U.S. Pat. No. 7,056,020, and entitled "ALIGNMENT SYSTEMS AND METHODS FOR RADIOGRAPHIC IMAGING SYSTEMS," which is incorporated in-full by reference herein.

FIELD OF THE INVENTION

The present invention relates generally to the medical imaging field. More specifically, the present invention relates to a method and apparatus for tomosynthesis image quality control. The method and apparatus address the measurement of in-plane resolution and slice thickness, via the measurement of modulation transfer function (MTF).

BACKGROUND OF THE INVENTION

With applications ranging from diagnostic procedures to radiation therapy, the importance of high-performance medical imaging is immeasurable. As such, advanced medical imaging technologies are continually being developed. Digital medical imaging technologies represent the future of medical imaging. Digital medical imaging systems produce far more accurate and detailed images of an anatomical object than conventional film-based medical imaging systems, and allow for the further enhancement of an image once an anatomical object is scanned.

Tomography is a two-dimensional radiographic imaging technique in which a cross-sectional image of a selected plane of an anatomical object is obtained, while details in other planes of the anatomical object are blurred. Tomosynthesis is an advanced application in radiographic imaging that allows for the retrospective reconstruction of an arbitrary number of tomographic planes of anatomy from a set of low-dose projection images acquired over a limited angle. The depth information carried by these tomographic planes is unavailable in conventional projection x-ray imaging. In other words, tomosynthesis is an advanced three-dimensional radiographic imaging technique in which several two-dimensional images of an anatomical object are obtained at different angles and/or planes. These two-dimensional images are then reconstructed as a three-dimensional image of the volume of the anatomical object. Unlike conventional projection x-ray imaging techniques, tomosynthesis provides depth information about an area of interest within an anatomical object being imaged, such as a tumor or other anatomical feature. Tomosynthesis enables any number of two-dimensional tomographic image slices to be reconstructed from a single scanning sequence of x-ray exposures, without requiring additional x-ray imaging, thereby making tomosynthesis a desirable characterization tool.

Typically, in digital tomography systems, an x-ray source is positioned on one side of an anatomical object to be imaged, while an x-ray detector (i.e., an amorphous silicon flat panel x-ray detector) is positioned on the opposite side of the anatomical object to be imaged. In amorphous silicon flat panel x-ray detectors, an amorphous silicon array is disposed on a glass substrate and a scintillator is disposed over, and is optically coupled to, the amorphous silicon array. The x-ray source sweeps along a line, arc, circle, ellipse, hypocycloid, or any other suitable geometry, directing a beam of x-ray photons towards the scintillator. The scintillator absorbs the x-ray photons and converts them to visible light. The amorphous silicon array then detects the visible light and converts it into an electrical charge at each pixel. The electrical charge at each pixel of the amorphous silicon array is read out and digitized by low-noise electronics, and is then sent to an image processor. Finally, a two-dimensional cross-sectional image is displayed on a display, and may be stored in a memory for later retrieval. A series of two-dimensional cross-sectional images may be reconstructed using one or more three-dimensional reconstruction algorithms, if desired, to incorporate depth information into a final three-dimensional image.

With respect to digital tomography systems, accurate alignment of the x-ray source with respect to the x-ray detector is critical to adequate image resolution. Phantoms are often used for calibrating and/or validating the alignment of film-based x-ray systems, where it is difficult to quantify x-ray levels or signal levels accurately. However, one drawback associated with film-based x-ray systems is that, typically, they only allow for a visual assessment of image sharpness to be made. Digital radiographic imaging systems, such as digital tomography systems, and any other radiographic imaging systems that allow an image to be digitized for numerical analysis, lend themselves to allowing accurate quantitative measurements of the alignment and/or image resolution or sharpness to be obtained. Accordingly, U.S. patent application Ser. No. 10/755,074, filed on Jan. 9, 2004, and entitled "ALIGNMENT SYSTEMS AND METHODS FOR RADIOGRAPHIC IMAGING SYSTEMS," which is incorporated in-full by reference herein, provides systems and methods, and simple geometric-shaped phantoms, that utilize discrete spatial and frequency analysis to accurately quantify the mechanical alignment of radiographic imaging systems, thereby allowing for the precise mechanical alignment thereof so that optimal image resolution can be obtained therefrom.

With respect to digital tomosynthesis systems, there are two important image quality characteristics: in-plane resolution and slice thickness. In-plane resolution defines a system's capability to resolve adjacent anatomical objects or anatomical features disposed only a small distance apart in the same plane. As an example, referring to FIG. 1, which illustrates (or closely approximates) a standard line pair phantom 10, well known to those of ordinary skill in the art, higher in-plane resolution means that a system is capable of resolving more line pairs 12. In a clinical context, this means that subtle structures, such as capillaries, microcalcifications, or the like, are capable of being resolved.

Slice thickness, on the other hand, defines a system's resolving power between different planes. Conventionally, radiographic images reflect two-dimensional projections of three-dimensional anatomical objects and, thus, it is difficult to understand the spatial relationship between anatomical features. Because the image quality signature test (IQST) in current imaging products is designed to measure only in-plane resolution, bad pixels, and other detector-specific metrics, it is not suitable for the measurement of slice thickness. Considering the tomosynthesis case, it is now possible to encode the depth information of overlapping/underlying anatomical features with images. As compared to the tomography case, the definition of slice thickness is not obvious for the tomosynthesis case, because tomosynthesis planes lie perpendicular (or oblique) to the x-ray beams. In the tomography case, the image planes lie parallel (or nearly parallel, in the multislice tomography case) to the x-ray beams. Therefore, while tomography primarily employs direct measurement of slice thickness, both direct and indirect measurement are required for tomosynthesis.

Therefore, what is needed is an indirect method, and an associated apparatus, for measuring in-plane resolution and slice thickness. Ideally, this method, and the associated apparatus, would be based on the measurement of modulation transfer function (MTF). Advantageously, such a method, and an associated apparatus, would combine both in-plane resolution and slice thickness in one measurement, be accurate and reliable, be easily automated, and not require costly phantoms.

BRIEF SUMMARY OF THE INVENTION

In various exemplary embodiments, the present invention provides a method and apparatus for tomosynthesis image quality control. More specifically, the present invention provides a method and apparatus that address the measurement of in-plane resolution and slice thickness, via the measurement of modulation transfer function (MTF). In practice, the method and apparatus of the present invention can be combined with any specially-designed tomosynthesis slice thickness phantom, existing today or in the future, in order to provide both quantitative and intuitive quality checks for a tomosynthesis system.

In one exemplary embodiment of the present invention, a method for tomosynthesis image quality control for a tomosynthesis imaging system, the method addressing the measurement of in-plane resolution and slice thickness, via the measurement of modulation transfer function (MTF), includes: positioning a phantom having an edge of predetermined sharpness at a predetermined angle relative to an imaging plane of an x-ray detector; performing tomosynthesis acquisition and generating one or more slice images using one or more three-dimensional reconstruction algorithms; selecting a slice image to be measured from the one or more slice images; identifying a sharpest edge in the slice image to be measured, wherein the sharpest edge in the slice image to be measured includes the in-focus portion of the phantom; inputting the slice image to be measured and coordinates of the sharpest edge in the slice image to be measured into an MTF algorithm; and, using the MTF algorithm, calculating the in-plane resolution and slice thickness of the slice image to be measured.

In another exemplary embodiment of the present invention, a method for tomosynthesis image quality control for a tomosynthesis imaging system, the method addressing the measurement of in-plane resolution and slice thickness, via the measurement of modulation transfer function (MTF), includes: positioning a phantom having an edge of predetermined sharpness at a predetermined angle relative to an imaging plane of an x-ray detector; performing tomosynthesis acquisition and generating one or more slice images using one or more three-dimensional reconstruction algorithms; selecting a slice image to be measured from the one or more slice images; identifying a sharpest edge in the slice image to be measured, wherein the sharpest edge in the slice image to be measured includes the in-focus portion of the phantom; inputting the slice image to be measured and coordinates of the sharpest edge in the slice image to be measured into an MTF algorithm; and, using the MTF algorithm, calculating the in-plane resolution and slice thickness of the slice image to be measured, wherein the MTF algorithm includes: extracting an edge profile from a reconstructed tomosynthesis plane; taking a first derivative of the edge profile; performing a Fourier transform on the first derivative of the edge profile to determine a spatial MTF for a predetermined distance along the phantom; calculating a half-width-at-half-maximum (HWHM) for the spatial MTF, the HWHM corresponding to the sharpness of the edge profile representing the in-plane resolution of the tomosynthesis imaging system; and determining the slice thickness of the tomosynthesis imaging system from a HWHM vs. z-direction curve.

In a further exemplary embodiment of the present invention, an apparatus for tomosynthesis image quality control for a tomosynthesis imaging system, the apparatus addressing the measurement of in-plane resolution and slice thickness, via the measurement of modulation transfer function (MTF), includes: a phantom having an edge of predetermined sharpness positioned at a predetermined angle relative to an imaging plane of an x-ray detector; means for performing tomosynthesis acquisition and generating one or more slice images using one or more three-dimensional reconstruction algorithms; means for selecting a slice image to be measured from the one or more slice images; means for identifying a sharpest edge in the slice image to be measured, wherein the sharpest edge in the slice image to be measured includes the in-focus portion of the phantom; means for inputting the slice image to be measured and coordinates of the sharpest edge in the slice image to be measured into an MTF algorithm; and means for, using the MTF algorithm, calculating the in-plane resolution and slice thickness of the slice image to be measured.

BRIEF DESCRIPTION OF THE DRAWINGS

The method and apparatus of the present invention are illustrated and described herein with reference to the various drawings, in which like reference numbers denote like method steps and/or apparatus components, as appropriate, and in which.

DETAILED DESCRIPTION OF THE INVENTION

For the purpose of promoting a thorough understanding of the present invention, reference will now be made to various preferred embodiments of the invention, as illustrated in FIGS. 1-13, and specific language used to describe the same. The terminology used herein is for the purpose of description, and not of limitation. Specific structural and functional details disclosed herein are not to be interpreted as limiting, but merely as a basis for the claims, and as a representative basis for teaching one of ordinary skill in the art to variously employ the invention. Any modifications to or variations in the depicted structures and functions, and such further applications of the principles of the invention as illustrated herein, as would normally occur to one of ordinary skill in the art, are considered to be within the spirit and scope of the invention.

Figure 1:
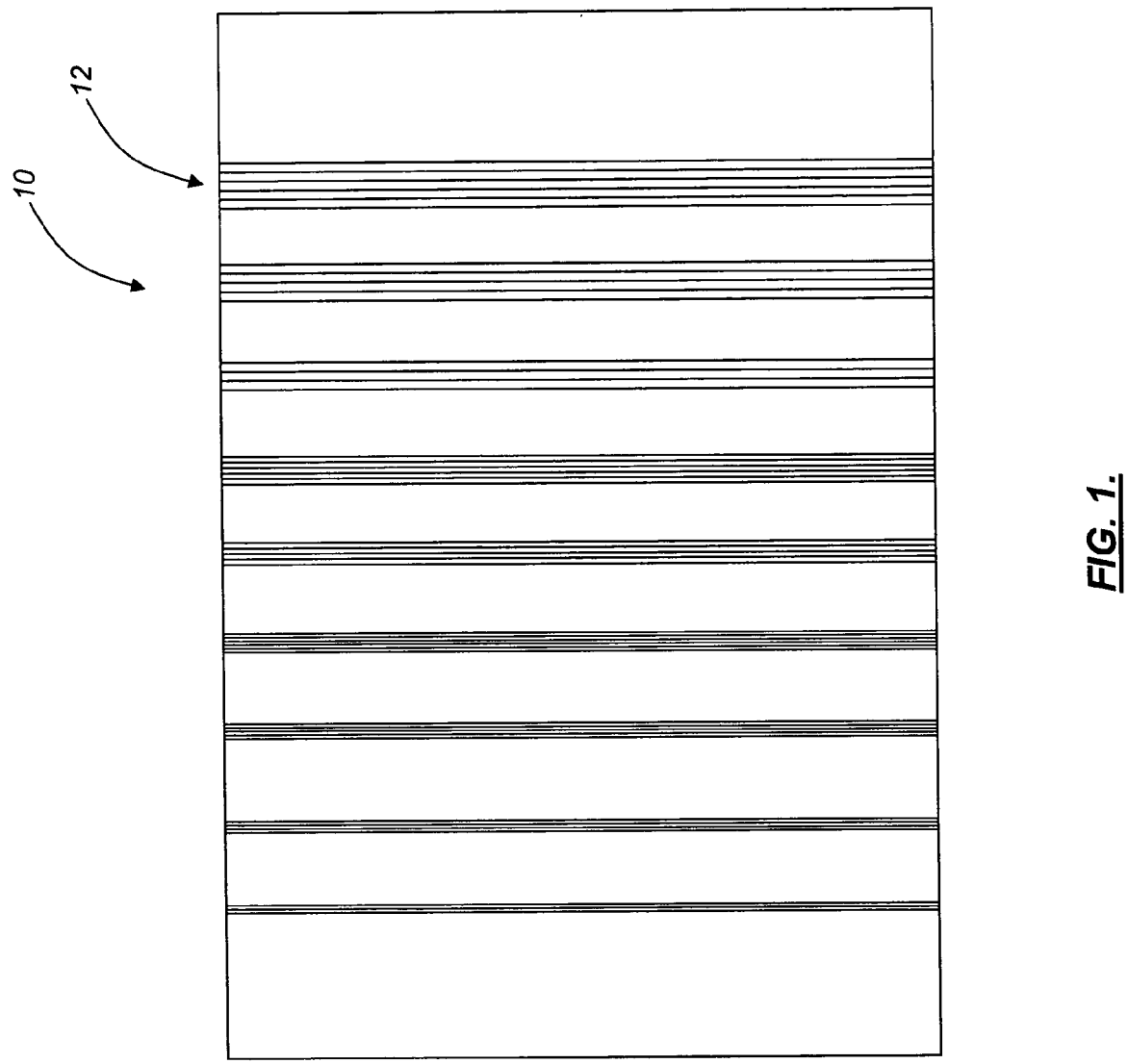
FIG. 1 is a schematic diagram illustrating (or closely approximating) a standard line pair phantom, well known to those of ordinary skill in the art, used to assess and quantify the in-plane resolution of a radiographic imaging system.
Figure 2:
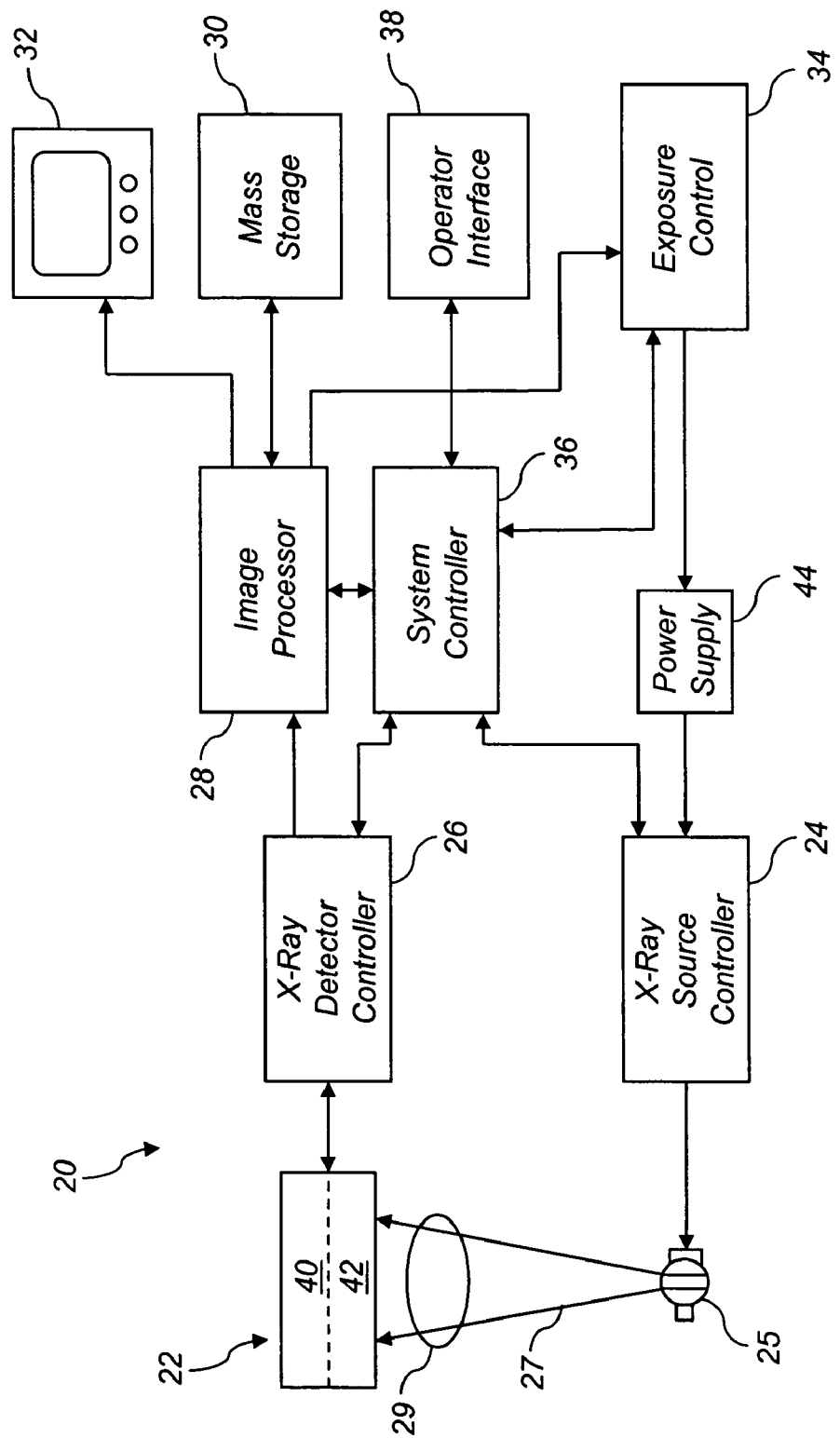
FIG. 2 is a schematic diagram illustrating the architecture of one exemplary digital tomography system, as utilized in embodiments of the present invention.

Referring to FIG. 2, there is illustrated a schematic diagram showing the architecture of one exemplary digital tomography system 20, as utilized in embodiments of the present invention. A digital tomography system 20 typically includes an x-ray source 25, an x-ray detector 22, an x-ray detector controller 26 that incorporates electronics for operating the x-ray detector 22, and an x-ray source controller 24 that incorporates electronics for operating the x-ray source 25. In operation, an overall system controller 36 provides power and timing signals to the x-ray source controller 24, which then controls the operation, position, projection/shooting angle, sweeping speed, etc. of the x-ray source 25. The x-ray source 25 typically sweeps along a line, arc, circle, ellipse, hypocycloid, or any other suitable geometry, while x-rays 27 are directed from the x-ray source 25 towards the x-ray detector 22, which comprises an amorphous silicon array 40 and a scintillator 42. The overall system controller 36 also controls the operation of the x-ray detector controller 26, which then controls the operation of the x-ray detector 22. After passing through an anatomical object being imaged (i.e., a patient 29), the x-rays 27 strike the scintillator 42, which converts the x-ray photons therein to visible light. The visible light is then converted to an electrical charge by an array of photodiodes 51 (FIG. 3) in the amorphous silicon array 40. Each photodiode 51 is of large enough area to ensure that it will intercept a sizeable portion of the visible light produced by the scintillator 42. Each photodiode 51 also has a relatively large capacitance that allows it to store the electrical charge that results from the visible light photon excitation. A data acquisition system within the x-ray detector controller 26 samples analog electrical charge data from the x-ray detector 22, and converts that analog electrical charge data to digital signals for subsequent processing. The digital signals are sent to an image processor 28, where the image signal is processed and enhanced. The processed and enhanced image may then be displayed on a cathode ray tube display 32, or other suitable display, and/or the image can be stored in mass storage 30 for later retrieval. Optionally, the image processor 28 also produces a brightness control signal which can be applied to an exposure control circuit 34 to regulate the power supply 44, which thereby regulates the x-ray source 25 through the x-ray source controller 24. The operation of the digital tomography system 20 is governed by the overall system controller 36, which receives commands and/or scanning parameters from an operator via an operator interface 38. The operator interface 38 comprises, for example, a keyboard, touchpad, or other suitable input device. The cathode ray tube display 32 (or other suitable display) allows the operator to view the reconstructed image and other data from the image processor 28. The operator supplied commands and/or scanning parameters are used by the overall system controller 36 to provide control signals and information to the image processor 28, the x-ray source controller 24, the x-ray detector controller 26, and/or the exposure control circuit 34.

Embodiments of the present invention make use of software or firmware running on the overall system controller 36 to carry out the processing of data associated with the method and apparatus of the invention. A mouse, pointing device, or other suitable input device is employed to facilitate the entry of data and/or image locations, etc. Other embodiments of the present invention utilize a general-purpose computer or workstation having a memory device and/or printing capability for storing and/or printing images. Suitable memory devices are well known to those of ordinary skill in the art and include, but are not limited to, random-access memory (RAM), hard drives, optical media, diskettes, etc. Embodiments using general-purpose computers or workstations receive data therefrom via conventional electronic storage media and/or conventional communications links, and images are reconstructed therefrom.

Figure 3:
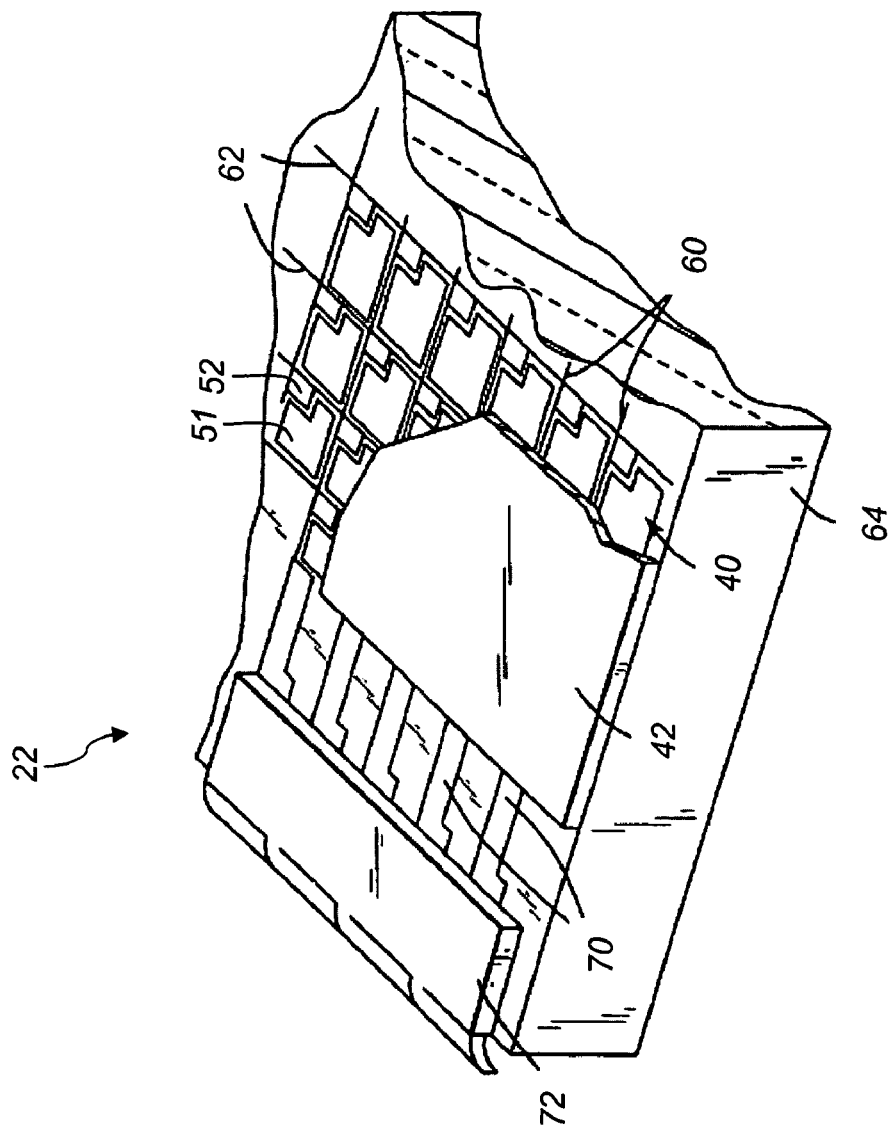
FIG. 3 is a perspective view illustrating an exemplary amorphous silicon flat panel x-ray detector, as utilized in embodiments of the present invention.

Referring to FIG. 3, there is illustrated an exemplary amorphous silicon flat panel x-ray detector 22, as utilized in embodiments of the present invention. Typically, column electrodes 60 and row electrodes 62 are disposed on a single-piece glass substrate 64, and an amorphous silicon array 40 is defined thereby. The amorphous silicon array 40 includes an array of photodiodes 51 and field effect transistors (FETs) 52. A scintillator 42 is disposed over the amorphous silicon array 40, and is optically coupled thereto. The scintillator 42, which may be, for example, a dose-efficient cesium iodide scintillator, receives and absorbs x-ray photons during operation, and converts the x-ray photons to visible light. The high-fill factor amorphous silicon array 40, within which each photodiode 51 represents a pixel, converts the detected visible light into an electrical charge at each pixel. The electrical charge at each pixel is then read out and digitized by low-noise electronics (via contact fingers 70 and contact leads 72), and is thereafter sent to the image processor 28 (FIG. 2).

Tomographic imaging systems produce an image having a slice thickness that is dependent upon the sweep angle that is used while the image is being acquired. The mechanical alignment and velocity tracking of the x-ray source 25 (FIG. 2) with respect to the x-ray detector 22 (FIGS. 2 and 3) are critical to precise slice thickness and slice depth in the image. However, it is relatively difficult to directly measure the numerous items that contribute to this mechanical alignment. Therefore, a good alternative measurement of the mechanical alignment of such systems, as well as other radiographic imaging systems, is obtained by indirectly measuring the resulting quality of an image of a known phantom.

Phantoms are commonly used with film-based imaging systems to determine the image quality of a resulting image. However, using such phantoms with film-based systems typically only allows for the qualitative, or subjective, analysis of the resulting image quality or sharpness, and indicates only whether the slice thickness and slice depth are approximately correct. Detailed quantitative analytical results are relatively difficult to obtain, and are beyond the reach of most conventional systems and methods.

Currently, there are no acceptable systems and methods for quantitatively evaluating the mechanical alignment of radiographic imaging systems, and the resolution of the resulting images created thereby. The phantoms and discrete spatial and frequency analysis methods of U.S. patent application Ser. No. 10/755,074, filed on Jan. 9, 2004, and entitled "ALIGNMENT SYSTEMS AND METHODS FOR RADIOGRAPHIC IMAGING SYSTEMS," which is incorporated in-full by reference herein, provide for the quantitative analysis of the mechanical alignment of radiographic imaging systems, thereby allowing such imaging systems to be precisely aligned so that optimal image quality can be achieved.

The resolution of an x-ray detector can be measured using a thin radio-opaque bar-shaped phantom that is placed on the surface of the x-ray detector. An x-ray image thereof is acquired, and a subset of the image is analyzed by taking the Fast Fourier Transform (FFT) of the derivative of the edge that is formed by the image of the bar. The result of this calculation provides the spatial frequency response of the imaging system, which is one way to define the resolution of the imaging system.

One or more simple geometric-shaped phantoms can be used to determine the focal depth and focal range of a radiographic imaging system. The phantoms of the present invention include any suitable radio-opaque attenuating material that is capable of holding an edge straight enough to allow image resolution measurements and the like to be obtained thereof.

Figure 4:
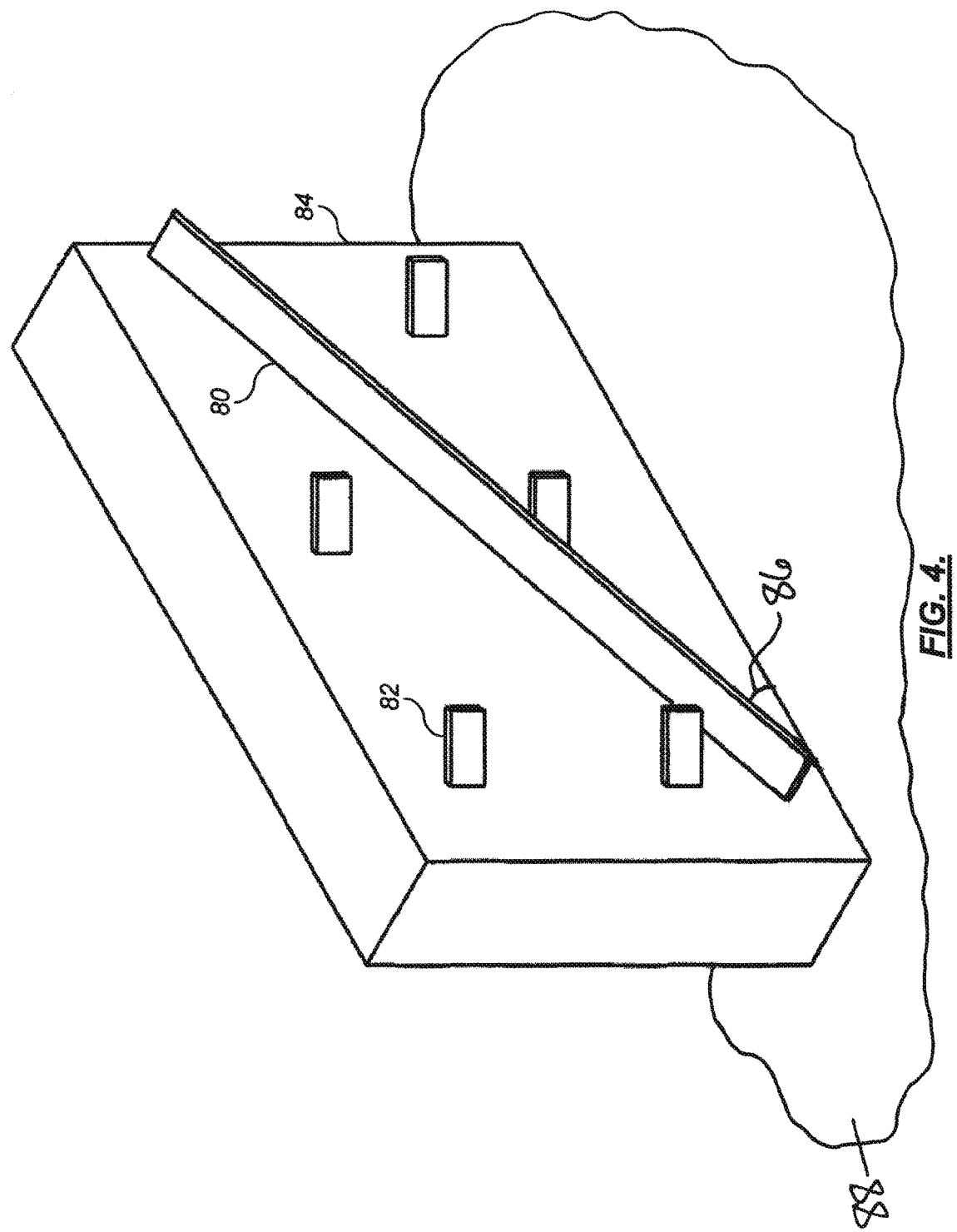
FIG. 4 is a perspective view illustrating an exemplary radio-translucent support and bar-shaped "ramp" phantom, as utilized in embodiments of the present invention.
Figure 5:
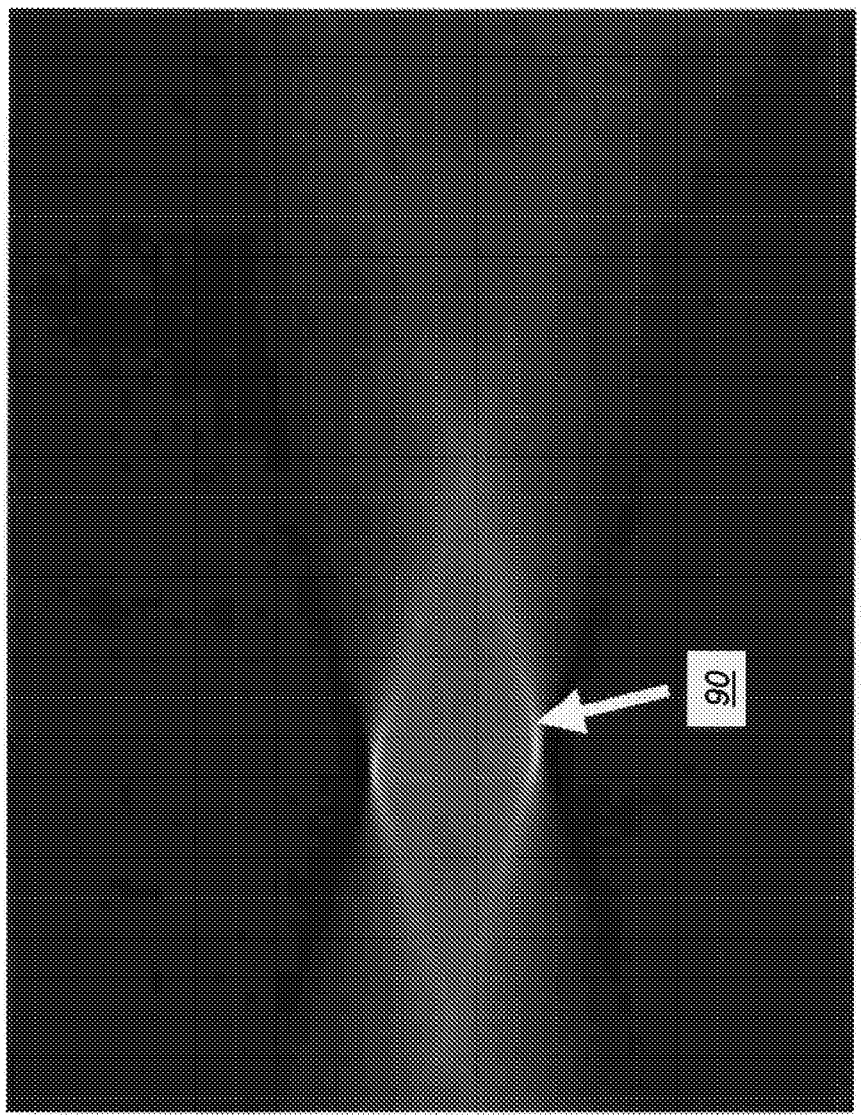
FIG. 5 is a tomographic reconstructed slice image of the ramp phantom of FIG. 4, with the sharpest point (the brightest point) highlighted.

Some exemplary, non-limiting, materials include tungsten, lead, tin, lead-tin alloys, steel, and epoxy impregnated with a high atomic number filler. Referring to FIG. 4, embodiments of the present invention utilize a radio-translucent support 84 disposed adjacent to the x-ray detector 22 (FIGS. 2 and 3), wherein the radio-translucent support 84 has a thin bar-shaped "ramp" phantom 80 positioned thereon or therein at an angle 86 relative to the imaging plane 88 of the x-ray detector 22, such that the center of the ramp phantom 80 is at or near the center of the imaging system 20 (FIG. 2). This radio-translucent support 84 consists of any suitable radio-translucent material, such as, for example, low-density foam (to simulate air), water, or any suitable human tissue-like material. The long axis of the ramp phantom 80 is arranged perpendicular to the direction of travel of the x-ray source 25 (FIG. 2) and/or the x-ray detector 22, such that the resulting image provides the best resolution at the focal depth of the imaging system 20. For example, the ramp phantom 80 can consist of a 1-mm tungsten "ruler" placed at a 30-degree angle 86 relative to the imaging plane 88 of the x-ray detector 22 face plate (not illustrated). The scanning direction is perpendicular to this ruler.

As described above, the present invention provides a method and apparatus for tomosynthesis image quality control. More specifically, the present invention provides a method and apparatus that address the measurement of in-plane resolution and slice thickness, via the measurement of modulation transfer function (MTF). In practice, the method and apparatus of the present invention can be combined with any specially-designed tomosynthesis slice thickness phantom, existing today or in the future, in order to provide both quantitative and intuitive quality checks for a tomosynthesis system.

The method of the present invention includes, as also described above, positioning a ramp phantom 80 (FIG. 4), which is made of high-density metal, tungsten, steel, etc., and which has a sharp edge, at an angle to the x-ray detector plane. Again, the radio-translucent support 84 utilized consists of low-density foam (to simulate air), water, or any suitable human tissue-like material. Next, tomosynthesis acquisition is performed and slice images are generated using one or more three-dimensional reconstruction algorithms. One or more slice images are used for subsequent measurement. Next, the sharpest edge in the image to be measured is identified, this edge representing the in-focus portion of the ramp phantom 80. This is illustrated in the tomographic reconstructed slice image of the ramp phantom of FIG. 5, with the sharpest point 90 (the brightest point) highlighted. This identification can be done manually by an operator, or using an automated software program. Next, the image to be measured and the coordinates of the sharpest point 90 are input into the algorithm of the present invention (or an equivalent algorithm) for calculating MTF.

Figure 6:
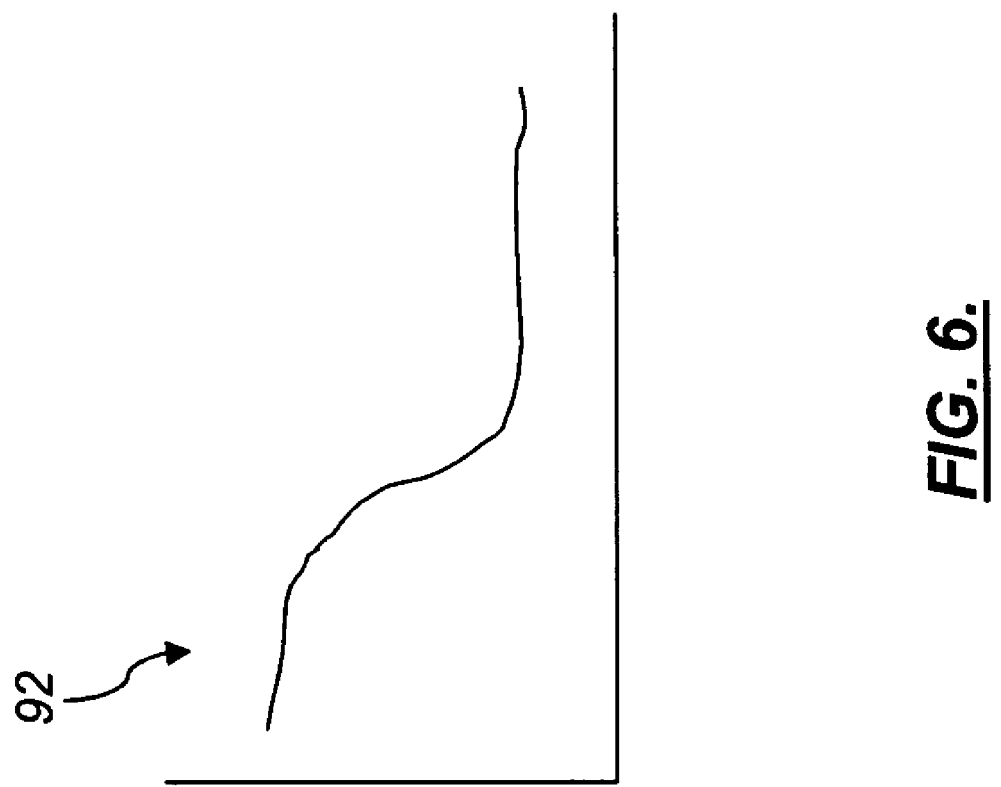
FIG. 6 is a plot of an edge profile, as utilized in embodiments of the present invention.
Figure 7:
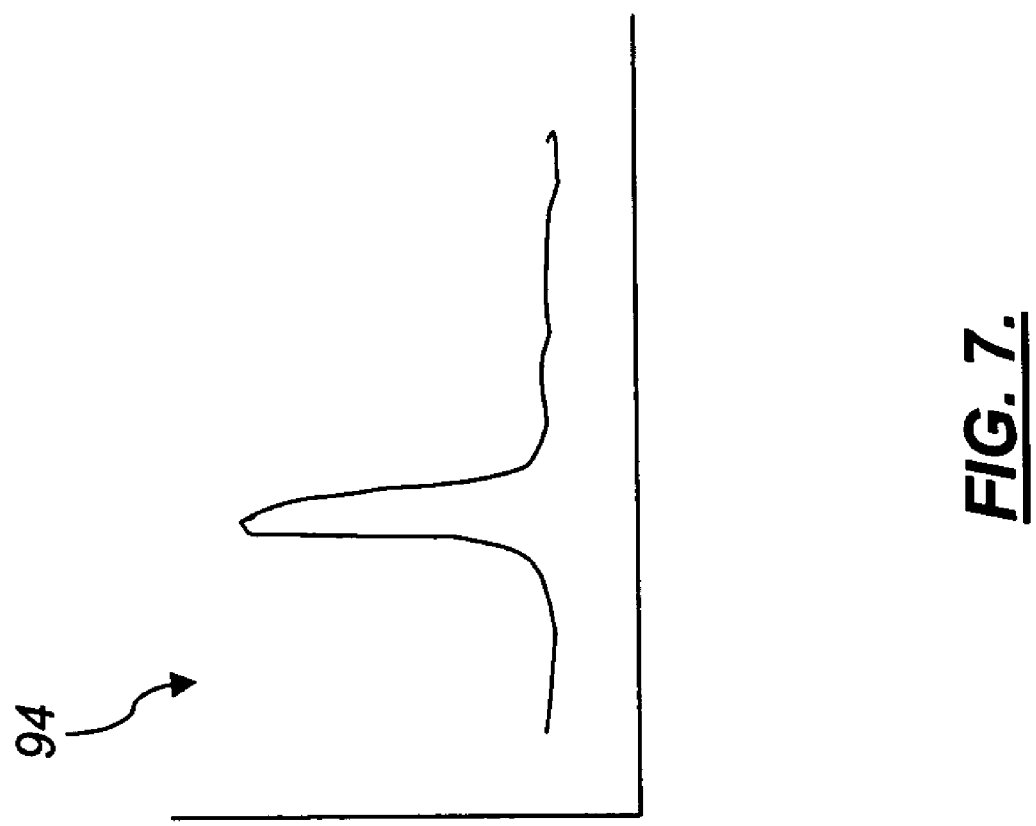
FIG. 7 is a plot of a first derivative of an edge profile, as utilized in embodiments of the present invention.
Figure 8:
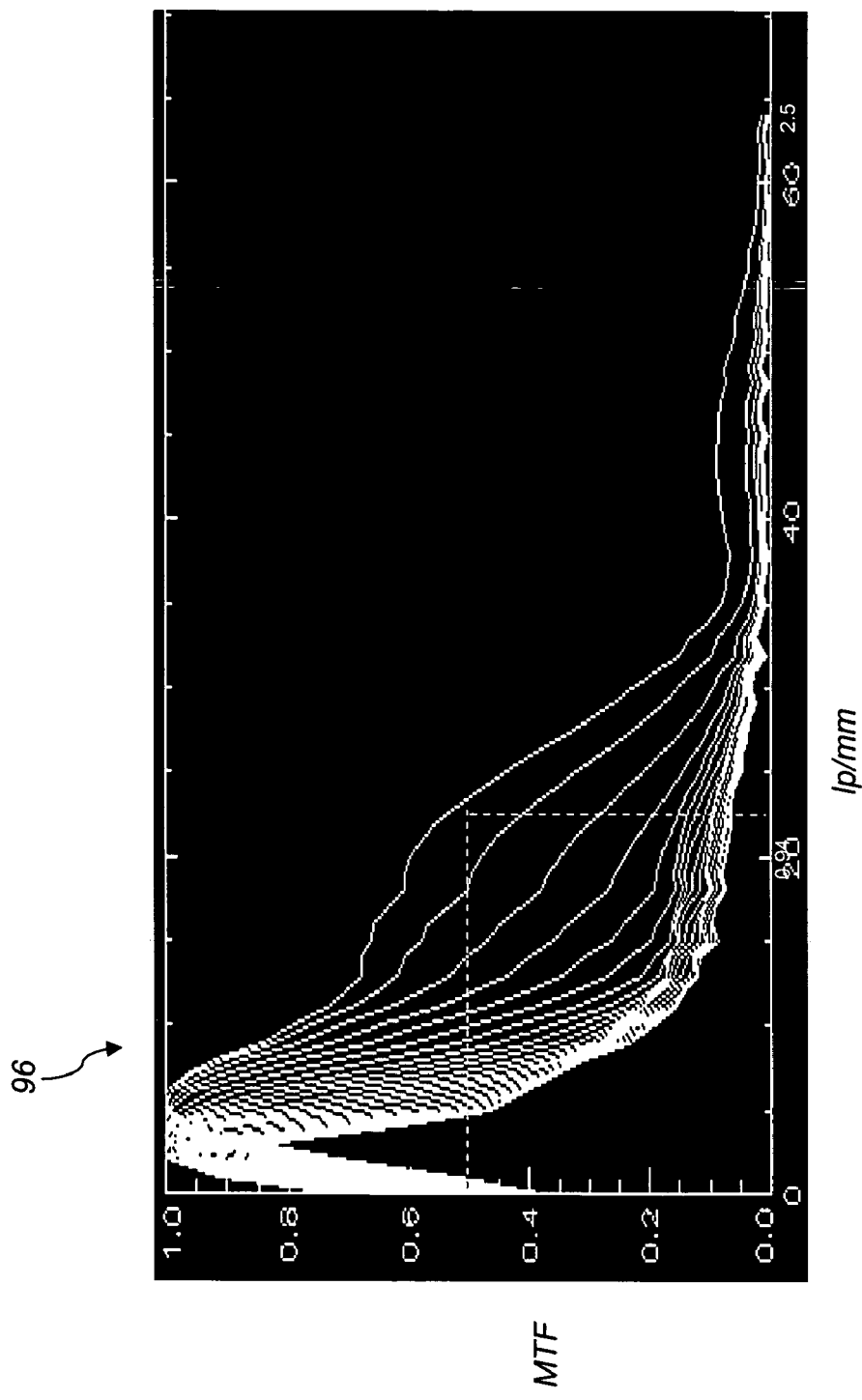
FIG. 8 is a plot of the spatial modulation transfer function (MTF) which identifies the half-width-at-half-maximum (HWHM) for each MTF, as utilized in embodiments of the present invention.
Figure 9:
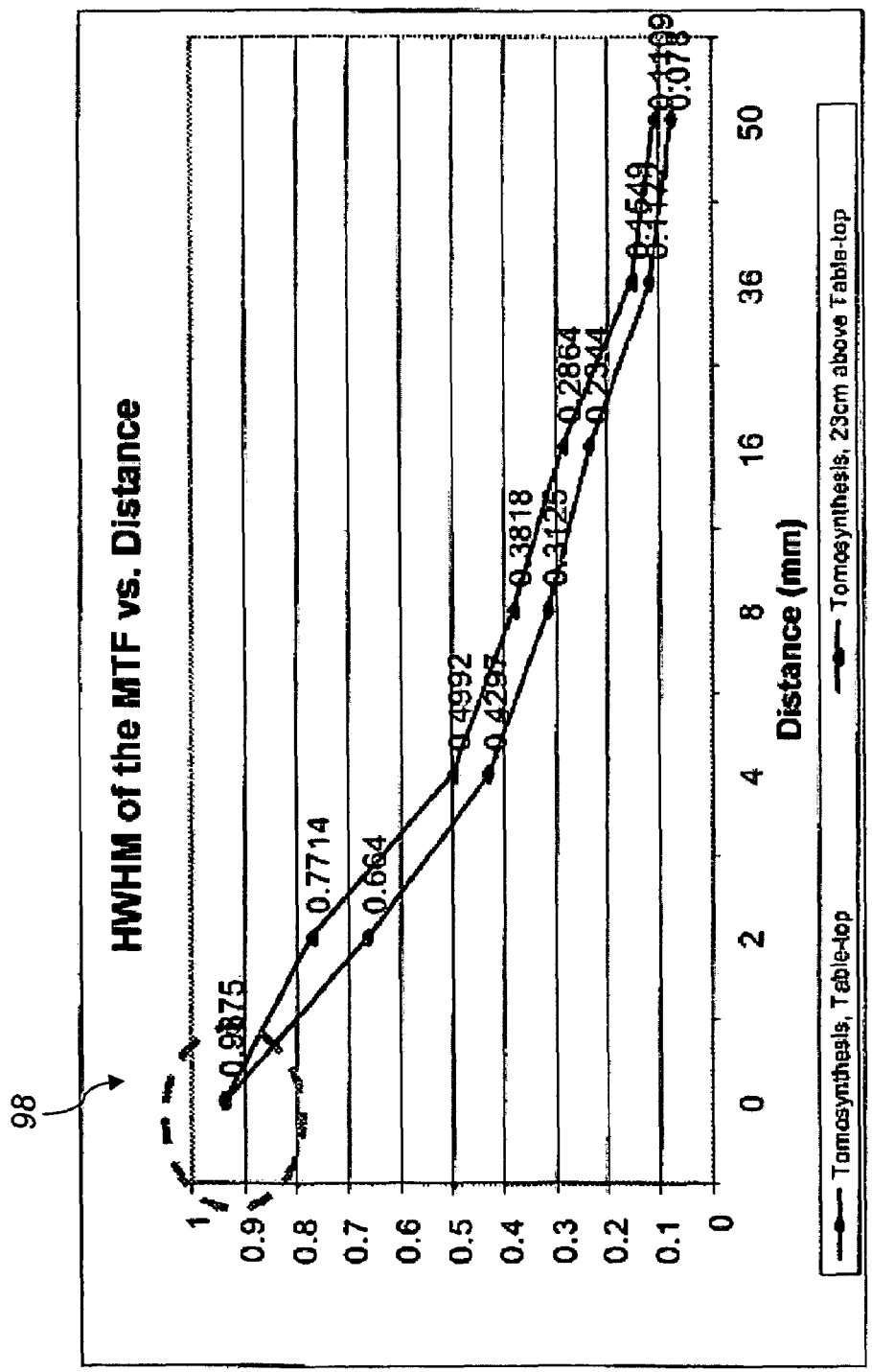
FIG. 9 is a plot illustrating the determination of the slice thickness of the tomosynthesis system from the HWHM vs. z-direction curve.

First, a series of edge profiles 92 are extracted from predetermined reconstructed tomosynthesis planes. One such edge profile 92 is illustrated in FIG. 6. The first edge profile 92 is selected to be across the sharpest point (in focus or in plane) on the edge. Other profiles are then selected that run parallel to the first and are spaced along the image of the ramp at 1 mm intervals, for example. Second, the first derivative 94 of each edge profile 92 is taken. This is illustrated in FIG. 7. Third, a Fourier transform is performed on the first derivative 94 of each edge profile 92 to determine the spatial MTF for that distance along the image of the ramp. The distance is then translated into the depth in the z-direction based upon the ramp angle. Fourth, the half-width-at-half-maximum (HWHM) 96 is calculated for each spatial MTF. This is illustrated in FIG. 8. Finally, the HWHM 96 corresponding to the sharpest edge profile 92 represents the in-plane resolution of the tomosynthesis system. The slice thickness of the tomosynthesis system is determined from the HWHM vs. z-direction curve 98. This is illustrated in FIG. 9.

The calculated in-plane resolution and slice thickness are reported to the operator via a display device and/or recording means (i.e., a storage device and/or printer). The above steps can be combined with any direct measurement of in-plane resolution/slice thickness using a specially-designed phantom, such as, for example, a thin wire or the like, to provide an intuitive understanding/visualization of the results. Regardless of the phantom(s) used, this intuitive understanding/visualization is achieved through one or more slice images of the phantom(s). Individually, or combined with previous steps, the specially-designed phantom(s) can be used to measure the contrast, low-contrast detectability, and noise properties (signal-to-noise ratio (SNR), noise spectrum, etc.) of the tomosynthesis system.

Returning now to the tomography case, and referring again to FIG. 4, a static reference image of the ramp phantom 80 can be taken to provide the maximum resolution possible for a particular height in question. The focal spot and inherent x-ray detector resolution, as well as the scatter from any attenuating material, can then be determined and later removed from the images. The analysis tools of the present invention can be used in any suitable direction (i.e., laterally, longitudinally, etc.).

Figure 10:
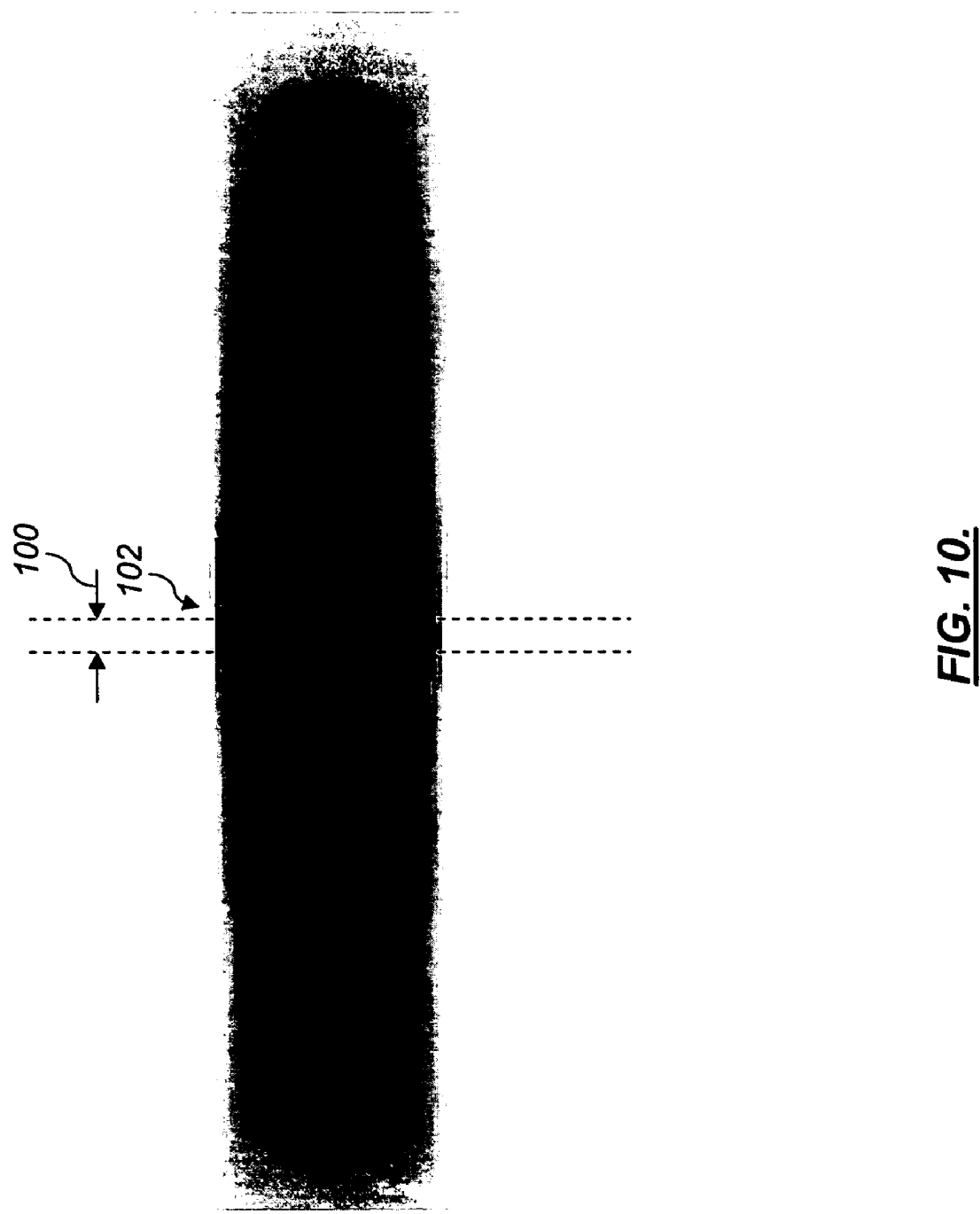
FIG. 10 is another tomographic reconstructed slice image of the ramp phantom of FIG. 4.

As illustrated in FIG. 10, the bow-tie-shaped image is the resulting tomographic image of the ramp phantom 80 (FIG. 4). The center of this image 100 represents the maximum possible resolution, and corresponds to the focal plane of the imaging system where the edge of the bar is well defined. The edge of the bar begins to blur as the distance from the focal plane increases. The increase in blurring from this maximum possible resolution at the focal plane is determined by the sweep angle used during image acquisition. Ideally, there should be a step change between the signal where the phantom is and the false signal where the phantom is not, in the vicinity of arrow 102. However, in reality, there will not be a step change near arrow 102 because mechanical misalignment issues cause the imaging system resolution to be less than perfect. So, in reality, what is observed is a rectangular profile having softened edges instead of sharp edges.

Figure 11:
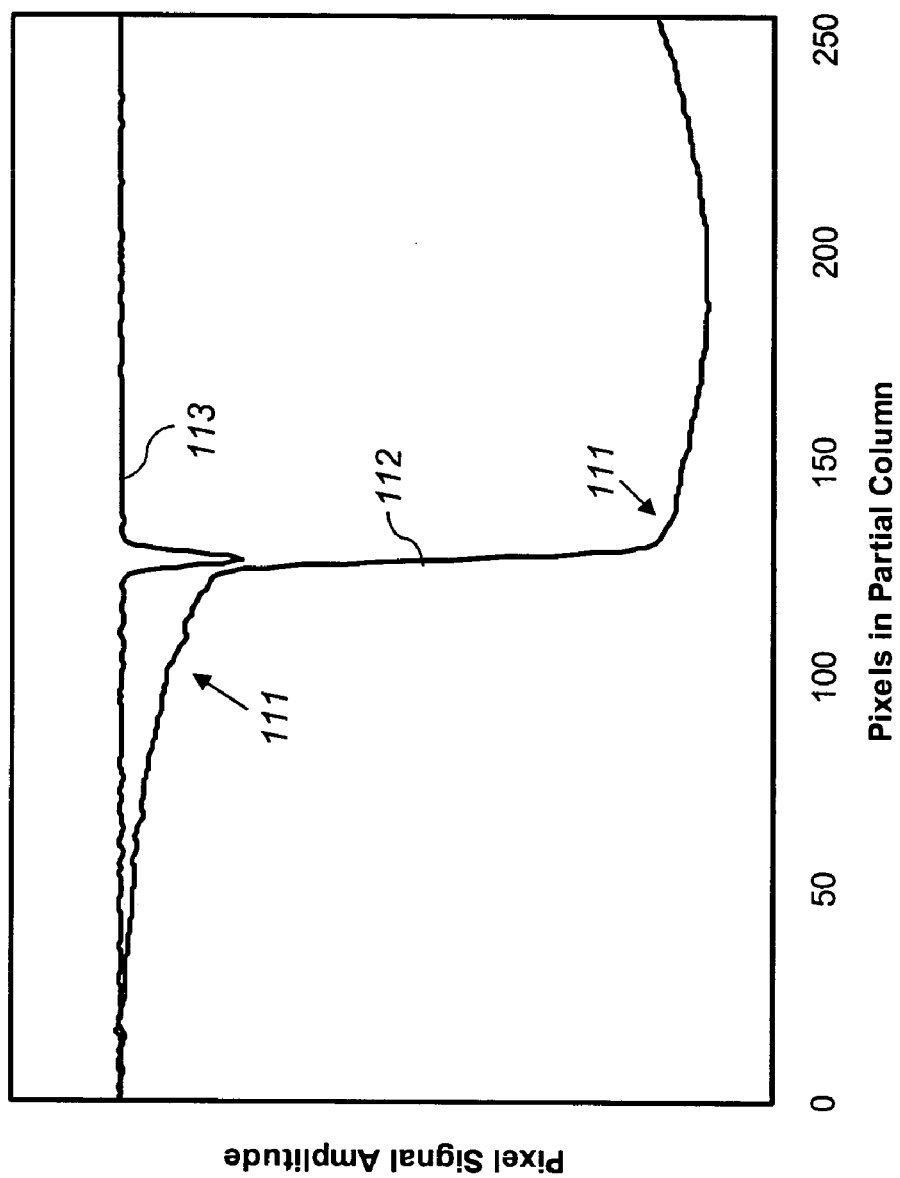
FIG. 11 is a plot illustrating a cross-sectional profile of the ramp phantom of FIG. 4 near the focal plane of the digital tomographic imaging system.

Referring now to FIG. 11, there is illustrated a cross-sectional profile 112 of one edge of the ramp phantom 80 (FIG. 4) near the focal plane of the digital tomographic imaging system. Ideally, if the ramp phantom 80 is precisely aligned to the centerline of the x-ray source and/or x-ray detector sweep, this profile 112 would have a rectangular shape with sharp edges, not a rounded profile with soft edges, as shown at points 111. The focal spot blurs the edges 111 of the phantom 80 to a certain degree, but the mechanical misalignments between the x-ray source 25 (FIG. 2) and the x-ray detector 22 (FIGS. 2 and 3) cause the bulk of the degradation of this image. The derivative of this profile shows the line spread function 113 of this digital tomographic imaging system.

Figure 12:
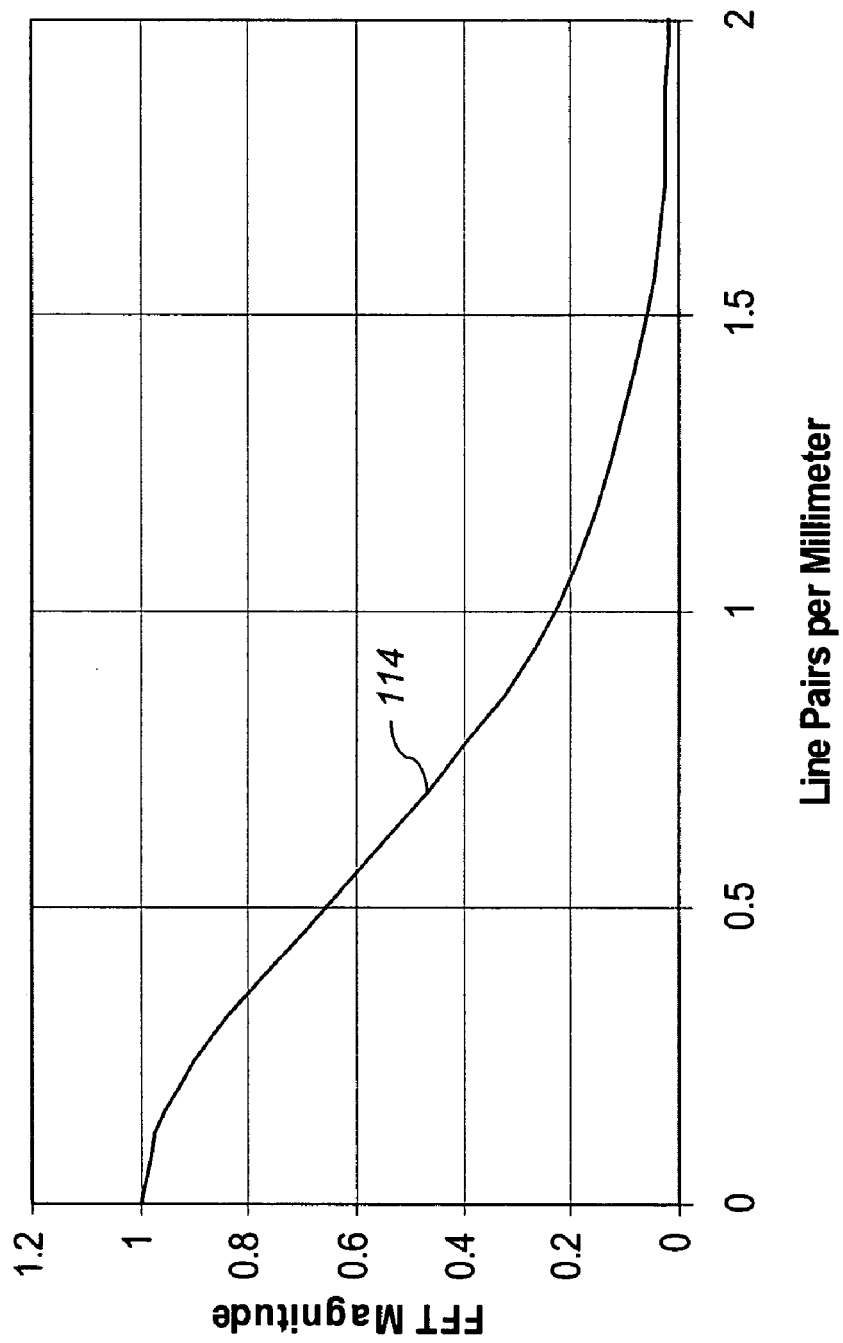
FIG. 12 is a plot illustrating a spatial frequency response at the focal plane of the digital tomographic imaging system.

Referring now to FIG. 12, there is illustrated the spatial frequency response 114 at the focal plane of the digital tomographic imaging system, which is one way to define the resolution of an imaging system. The spatial frequency response can be obtained by taking the Fast Fourier Transform (FFT) or other numerical analysis of the line spread function 113 (FIG. 11). Obtaining a numerical measure of the image resolution allows precise alignments and calibrations to be made to the digital imaging system so that the best possible images can be obtained therefrom.

As illustrated in FIG. 4, embodiments of the present invention can incorporate several smaller phantoms 82 that are useful for measuring the focal uniformity over a larger section of the detector area. The same analysis that was described for the ramp phantom 80 can be used for each of these smaller phantoms 82. Such embodiments provide an accurate measurement of the focal uniformity of the x-ray detector 22 (FIGS. 2 and 3) across a fixed focal depth.

Figure 13:
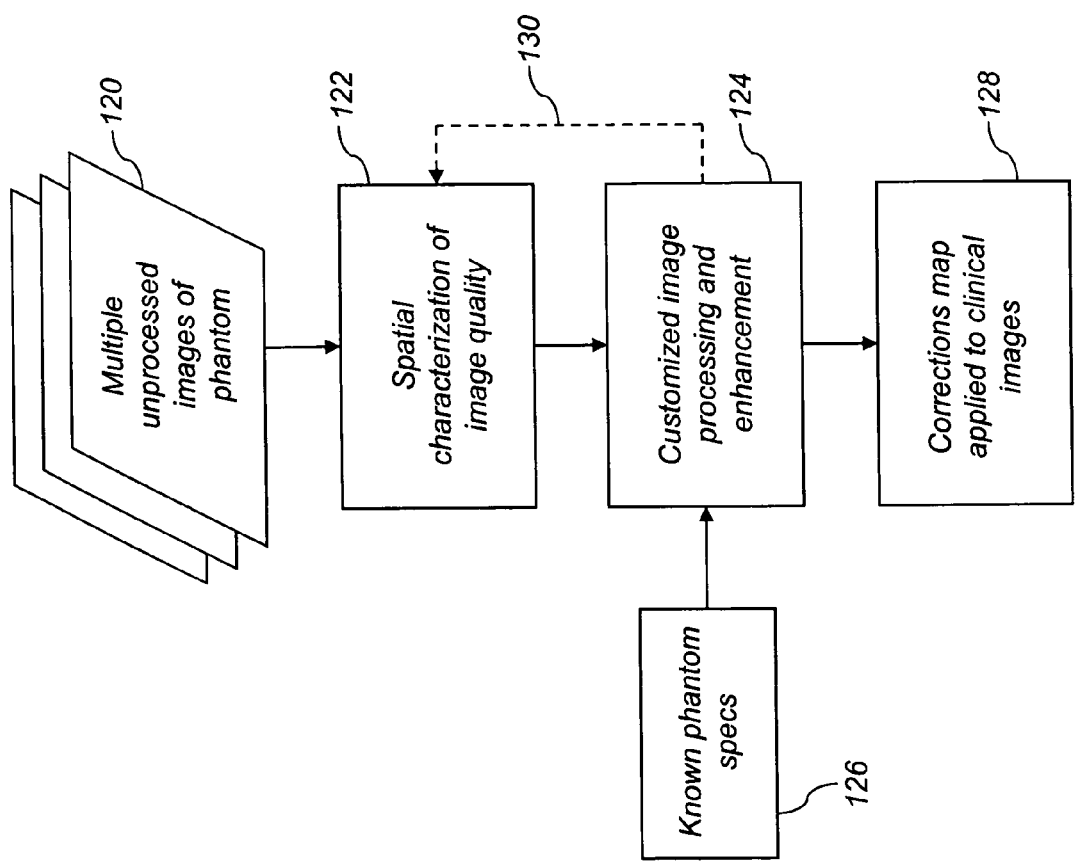
FIG. 13 is a flowchart illustrating one embodiment of a method of the present invention for correcting, using image processing and filtering techniques, repeatable alignment errors in order to yield uniform image quality for maximum visualization of anatomical objects that are imaged.

In addition to characterizing image quality performance at different locations within an image, the output of the analysis of the present invention can be used to correct, using image processing and filtering techniques, repeatable alignment errors in order to yield uniform image quality for maximum visualization of anatomical objects that are imaged. As illustrated in FIG. 13, to isolate repeatable alignment errors from random alignment errors, multiple unprocessed images of the phantom(s) are used 120. A spatial characterization of each image is made 122. Thereafter, customized image processing and enhancements are made 124, and take into account known phantom specifications 126 that have been previously determined. The image processing parameters are adjusted as necessary 130 to optimize the image quality. Finally, a corrections map is applied to the images 128, to produce final images that are free of repeatable alignment errors.

The phantoms, apparatuses, systems, and methods described herein can be used in numerous radiographic imaging systems, for purposes such as, but not limited to, medical imaging (i.e., film-based x-ray systems, digital x-ray systems, linear tomography systems, tomosynthesis systems, computed radiography systems, and any other radiographic imaging systems and/or x-ray planographic imaging systems that allow the obtained images to be digitized so that numerical analysis can be made thereof, etc.), nondestructive imaging and/or testing of parts, and/or for detecting contraband (i.e., weapons, explosives, etc.).

Various embodiments of the present invention have been illustrated and described in fulfillment of the various needs that the invention meets. It should be recognized that these embodiments are merely illustrative of the principles of the various embodiments of the present invention. Numerous modifications thereof and adaptations thereto will be apparent to those of ordinary skill in the art without departing from the spirit and scope of the present invention. For example, while the embodiments illustrated and described herein utilize a bar-shaped phantom, numerous other shapes are possible without deviating from the spirit and scope of the invention, and all such variations are intended to be covered herein. Thus, it is intended that the present invention cover all suitable modifications and variations as fall within the scope of the following claims and their equivalents.

What is claimed is:

1. A method for tomosynthesis image quality control for a tomosynthesis imaging system, the method addressing the measurement of in-plane resolution and slice thickness, via the measurement of modulation transfer function (MTF), the method comprising:

positioning a phantom having an edge of predetermined sharpness at a predetermined angle relative to an imaging plane of an x-ray detector;

performing tomosynthesis acquisition and generating one or more slice images using one or more three-dimensional reconstruction algorithms;

selecting a slice image to be measured from the one or more slice images;

identifying a sharpest edge in the slice image to be measured, wherein the sharpest edge in the slice image to be measured comprises the in-focus portion of the phantom;

inputting the slice image to be measured and coordinates of the sharpest edge in the slice image to be measured into an MTF algorithm;

using the MTF algorithm, calculating the in-plane resolution and slice thickness of the slice image to be measured; and reporting the calculated in-plane resolution and slice thickness to an operator.

2. The method of claim 1, wherein the phantom comprises one or more of a high-density metal, tungsten, and steel.

3. The method of claim 1, wherein the phantom is disposed on or within a radio-translucent support.

4. The method of claim 3, wherein the radio-translucent support comprises one or more of a low-density foam, water, and a human tissue-like material.

5. The method of claim 1, wherein identifying the sharpest edge in the slice image to be measured comprises one of identifying the sharpest edge in the slice image to be measured manually and identifying the sharpest edge in the slice image to be measured using an automated software program.

6. The method of claim 1, wherein the MTF algorithm comprises:
extracting an edge profile from a reconstructed tomosynthesis plane;
taking a first derivative of the edge profile;
performing a Fourier transform on the first derivative of the edge profile to determine a spatial MTF for a predetermined distance along the phantom;
calculating a half-width-at-half-maximum (HWHM) for the spatial MTF, the HWHM corresponding to the sharpness of the edge profile representing the in-plane resolution of the tomosynthesis imaging system; and
determining the slice thickness of the tomosynthesis imaging system from a HWHM vs. z-direction curve.

7. The method of claim 6, wherein extracting the edge profile from the reconstructed tomosynthesis plane comprises extracting the edge profile from the reconstructed tomosynthesis plane across an in-focus or in-plane portion of the reconstructed tomosynthesis plane.

8. The method of claim 6, wherein extracting the edge profile from the reconstructed tomosynthesis plane comprises extracting the edge profile from the reconstructed tomosynthesis plane across a plane that is parallel to an in-focus or in-plane portion of the reconstructed tomosynthesis plane.

9. The method of claim 6, further comprising outputting the in-plane resolution and slice thickness of the tomosynthesis imaging system to an operator.

10. The method of claim 6, further comprising combining the in-plane resolution and slice thickness of the tomosynthesis imaging system with direct measurements of in-plane resolution and slice thickness obtained using the phantom.

11. A method for tomosynthesis image quality control for a tomosynthesis imaging system, the method addressing the measurement of in-plane resolution and slice thickness, via the measurement of modulation transfer function (MTF), the method comprising:
positioning a phantom having an edge of predetermined sharpness at a predetermined angle relative to an imaging plane of an x-ray detector;
performing tomosynthesis acquisition and generating one or more slice images using one or more three-dimensional reconstruction algorithms;
selecting a slice image to be measured from the one or more slice images;
identifying a sharpest edge in the slice image to be measured, wherein the sharpest edge in the slice image to be measured comprises the in-focus portion of the phantom;
inputting the slice image to be measured and coordinates of the sharpest edge in the slice image to be measured into an MTF algorithm; and
using the MTF algorithm, calculating the in-plane resolution and slice thickness of the slice image to be measured, wherein the MTF algorithm comprises:
extracting an edge profile from a reconstructed tomosynthesis plane;
taking a first derivative of the edge profile;
performing a Fourier transform on the first derivative of the edge profile to determine a spatial MTF for a predetermined distance along the phantom;
calculating a half-width-at-half-maximum (HWHM) for the spatial MTF, the HWHM corresponding to the sharpness of the edge profile representing the in-plane resolution of the tomosynthesis imaging system; and
determining the slice thickness of the tomosynthesis imaging system from a HWHM vs. z-direction curve; and
reporting the calculated in-plane resolution and slice thickness to an operator.

12. The method of claim 11, wherein the phantom comprises one or more of a high-density metal, tungsten, and steel.

13. The method of claim 11, wherein the phantom is disposed on or within a radio-translucent support.

14. The method of claim 13, wherein the radio-translucent support comprises one or more of a low-density foam, water, and a human tissue-like material.

15. The method of claim 11, wherein identifying the sharpest edge in the slice image to be measured comprises one of identifying the sharpest edge in the slice image to be measured manually and identifying the sharpest edge in the slice image to be measured using an automated software program.

16. The method of claim 11, wherein extracting the edge profile from the reconstructed tomosynthesis plane comprises extracting the edge profile from the reconstructed tomosynthesis plane across an in-focus or in-plane portion of the reconstructed tomosynthesis plane.

17. The method of claim 11, wherein extracting the edge profile from the reconstructed tomosynthesis plane comprises extracting the edge profile from the reconstructed tomosynthesis plane across a plane that is parallel to an in-focus or in-plane portion of the reconstructed tomosynthesis plane.

18. The method of claim 11, further comprising outputting the in-plane resolution and slice thickness of the tomosynthesis imaging system to an operator.

19. The method of claim 11, further comprising combining the in-plane resolution and slice thickness of the tomosynthesis imaging system with direct measurements of in-plane resolution and slice thickness obtained using the phantom.

20. An apparatus for tomosynthesis image quality control for a tomosynthesis imaging system, the apparatus addressing the measurement of in-plane resolution and slice thickness, via the measurement of modulation transfer function (MTF), the apparatus comprising:
a phantom having an edge of predetermined sharpness positioned at a predetermined angle relative to an imaging plane of an x-ray detector;
means for performing tomosynthesis acquisition and generating one or more slice images using one or more three-dimensional reconstruction algorithms;
means for selecting a slice image to be measured from the one or more slice images;
means for identifying a sharpest edge in the slice image to be measured, wherein the sharpest edge in the slice image to be measured comprises the in-focus portion of the phantom;
means for inputting the slice image to be measured and coordinates of the sharpest edge in the slice image to be measured into an MTF algorithm; and
means for, using the MTF algorithm, calculating the in-plane resolution and slice thickness of the slice image to be measured.

21. The apparatus of claim 20, wherein the phantom comprises one or more of a high-density metal, tungsten, and steel.

22. The apparatus of claim 20, wherein the phantom is disposed on or within a radio-translucent support.

23. The apparatus of claim 22, wherein the radio-translucent support comprises one or more of a low-density foam, water, and a human tissue-like material.

24. The apparatus of claim 20, wherein the means for identifying the sharpest edge in the slice image to be measured comprises one of means for identifying the sharpest edge in the slice image to be measured manually and means for identifying the sharpest edge in the slice image to be measured using an automated software program.

25. The apparatus of claim 20, wherein the MTF algorithm comprises:
   means for extracting an edge profile from a reconstructed tomosynthesis plane;
   means for taking a first derivative of the edge profile;
   means for performing a Fourier transform on the first derivative of the edge profile to determine a spatial MTF for a predetermined distance along the phantom;
   means for calculating a half-width-at-half-maximum (HWHM) for the spatial MTF, the HWHM corresponding to the sharpness of the edge profile representing the in-plane resolution of the tomosynthesis imaging system; and
   means for determining the slice thickness of the tomosynthesis imaging system from a HWHM vs. z-direction curve.

26. The apparatus of claim 25, wherein the means for extracting the edge profile from the reconstructed tomosynthesis plane comprises means for extracting the edge profile from the reconstructed tomosynthesis plane across an in-focus or in-plane portion of the reconstructed tomosynthesis plane.

27. The apparatus of claim 25, wherein the means for extracting the edge profile from the reconstructed tomosynthesis plane comprises means for extracting the edge profile from the reconstructed tomosynthesis plane across a plane that is parallel to an in-focus or in-plane portion of the reconstructed tomosynthesis plane.

28. The apparatus of claim 25, further comprising an output device for outputting the in-plane resolution and slice thickness of the tomosynthesis imaging system to an operator.

29. The apparatus of claim 25, further comprising means for combining the in-plane resolution and slice thickness of the tomosynthesis imaging system with direct measurements of in-plane resolution and slice thickness obtained using the phantom.

* * * * *